United States Patent

Petter et al.

[11] Patent Number: 5,840,041
[45] Date of Patent: Nov. 24, 1998

[54] DEVICE FOR MEASURING THE MECHANICAL PROPERTIES OF BIOLOGICAL TISSUE

[75] Inventors: Erwin Petter, Elversberg; Jörg-Uwe Meyer, St. Ingberg, both of Germany

[73] Assignee: Fraunhofer-Gesellschaft zur Foerderung der angewandten Forschung e.V., Munich, Germany

[21] Appl. No.: 816,996

[22] Filed: Mar. 14, 1997

Related U.S. Application Data

[63] Continuation of PCT/EP95/03546 Sep. 8, 1995.

[30] Foreign Application Priority Data

Sep. 16, 1994 [DE] Germany .................. 44 33 104.5

[51] Int. Cl.$^6$ ........................................................ A61B 5/05
[52] U.S. Cl. ....................... 600/547; 600/402; 600/552
[58] Field of Search ................................ 600/382, 383, 600/402, 547, 552

[56] References Cited

U.S. PATENT DOCUMENTS

| Re. 34,663 | 7/1994 | Seale | 600/587 |
| 3,789,834 | 2/1974 | Duroux | 600/547 |
| 4,682,608 | 7/1987 | De Rigal et al. | 600/587 |
| 4,727,330 | 2/1988 | Funk | 600/547 |

*Primary Examiner*—Max Hindenburg
*Assistant Examiner*—Charles Marmor, II
*Attorney, Agent, or Firm*—Evenson, McKeown, Edwards & Lenahan, P.L.L.C.

[57] ABSTRACT

An apparatus for measuring the mechanical properties of biological tissue and the use of the apparatus is provided. The apparatus generates a magnetic field by means of a coil system comprising a permanent magnet as the actuator and a conductive foil as the sensor.

21 Claims, 2 Drawing Sheets

DEVICE FOR MEASURING THE MECHANICAL PROPERTIES OF BIOLOGICAL TISSUE

This is a continuation of PCT application PCT/EP 95/03546, the entire contents of which are expressly incorporated herein by reference.

This application claims priority of German patent application 44 33 104.5 filed Sep. 16, 1994, the entire contents of which are expressly incorporated herein by reference.

BACKGROUND AND SUMMARY OF THE INVENTION

The present invention relates to a device for measuring the mechanical properties of biological tissue.

Measurements of mechanical properties (elasticity, friction, resonance) are frequently conducted in industry. An actuator makes the object to be measured vibrate (sometimes at several points). Subsequently the vibrations are measured at the same or at other points. Usually an electromagnetic vibrator is employed as the actuator and an acceleration recorder as the sensor. The analysis is utilized to test the mechanical behavior of the object to be measured in operation.

In biomedicine, it is also useful to determine the mechanical properties of tissue (see, for example, D. E. Thompson, H. Mg. Hussein, and R. Q. Peritt, "Point impedance Characterization of Soft Tissues In Vivo," In: Bioengineering and the Skin, R. Marks, P. Payne, eds., MTP Press England (1981); and German patent document DE-A-34 33 699.) However, often the methods used in industry cannot be applied for biomedical measurements. The tissue to be measured is not always easily accessible and the size of the structure to be tested is so small that it is impossible to dispose an acceleration recorder on it. The smallest acceleration recorder still weighs approximately 0.5 g, which may exceed the weight of the tissue. Thus, the recorder itself can influence the measuring results.

In connection with detecting motor activity in animals, evaluation of changes in the impedance of a resonance circuit caused by the relative movement between an animal marked with a metallic object and a coil of a resonance circuit are known (see German patent document DE-OS 21 57 825). In contrast, in the case of the present invention, biological tissue is set into vibration by means of a magnet in order to test the mechanical properties.

Furthermore, a device for determining visco-elastic properties of the skin in which the mechanical excitation occurs by means of a magnet and a coil system is known (see German patent document DE 34 33 699 A1). A reflector, the movement of which is opto-electronically evaluated, is used as the sensor.

There is needed, therefore, an apparatus for measuring the mechanical properties of biological tissue in which the measuring device does not influence the measured results. These needs are met according to the present invention.

In one embodiment, the invention provides an apparatus for measuring the mechanical properties of biological tissue. The apparatus uses a coil system for generating a magnetic field and a device for exciting the tissue mechanically by means of a permanent magnet as the actuator and of a conductive foil as the sensor. In a related embodiment, the device for mechanically exciting the tissue comprises a foil composed of a soft magnetic material acting as an actuator and simultaneously acting as a sensor. A conductive foil can be placed on the soft magnetic material which, in addition, influences the impedance of the coil system. In a preferred embodiment, the mass of the actuator and the sensor are less than 0.2 g, preferably less than 0.1 g.

The embodiments of the invention can be incorporated into other devices and used in numerous ways to measure properties of biological tissue. For example, the entire apparatus can be incorporated into an endoscope, with the foil being optionally designed as the distal end of the endoscope. In such an endoscope, an elastic foil can be disposed between the tissue to be examined and the conductive foil. Alternatively, the apparatus can be operably attached to a contact lens. Thus, the foil and the magnet being embedded in a contact lens to measure eye vibrations, for example.

One skilled in the art will recognize a number of advantageous aspects and embodiments of the invention. For example, the actuator and the sensor are of relatively small mass (less than about 0.1 g), making it possible to utilize them at sites that are inaccessible to conventional actuators and sensors. Due to the fact that the mass of the actuator and the sensor is so small, they hardly influence the measurement of dynamic mechanical properties.

In addition, the sensor and the actuator are placed on the object to be measured. There is no wiring between the sensor, the actuator, and the rest of the measurement system. Wiring interferes with measurement and, in biological applications, may involve the risk of infection. Other advantageous aspects and embodiments will be appreciated by one skilled in the art considering the disclosure as a whole.

The apparatus of the invention comprises two parts. The first part is connected to the to-be-measured object and comprises either:

1. a permanent magnet and a conductive coil (FIG. 1);
2. a soft magnetic, conductive or non-conductive foil; or
3. a soft magnetic foil and a conductive non-magnetic foil.

The second part comprises a coil system, which is inductively coupled to the first part. Therefore, it is placed in spatial proximity to the first part. In order to direct the magnetic field in a defined direction, the coil system is inserted in a shell type core made of ferrite or iron powder.

The magnet and the foils can be of such small size that they only weigh a few milligrams. Soft magnetic materials have the advantage that they can be structured better than permanent magnets. Moreover, the configuration can be selected as desired. Permanent magnets, on the other hand, have to have a specific length-width ratio to ensure stability.

Measurement can also be conducted by a soft magnetic non-conductive foil, in which only the magnetic polarization generated in the foil changes the impedance of the coil system. A conductive foil made of a non-magnetic material can be added to the soft magnetic foil, conductive or nonconductive, for example, by being placed on it by adhesion or gluing. In this case, the measuring effect is due to the vibration of both the magnetic foil (magnetic polarization and eddy currents) and by the conductive foil (eddy currents).

Other objects, advantages and novel features of the present invention will become apparent from the following detailed description of the invention when considered in conjunction with the accompanying drawings.

DETAILED DESCRIPTION OF THE DRAWINGS

Figure 1:
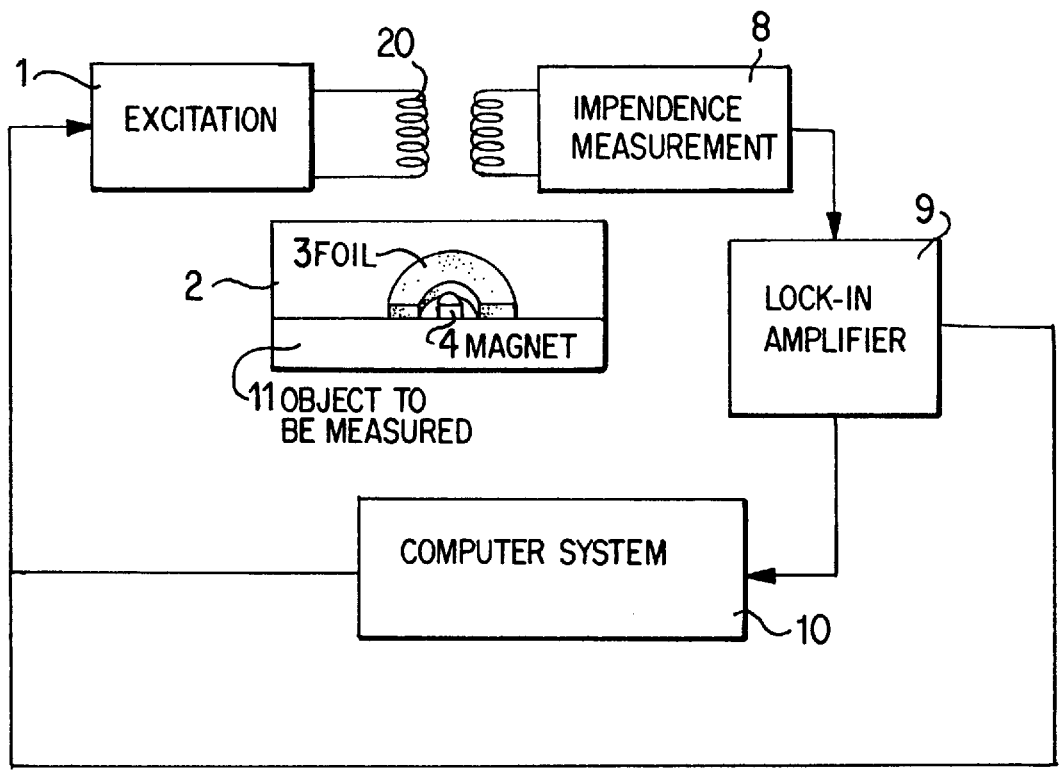
FIG. 1 shows a schematic of an apparatus for measuring the mechanical properties of the tissue.

In one embodiment of the invention, FIG. 1 shows a block diagram of a measurement system for measuring the mechanical properties of the tissue, in which the object to be measured is depicted only schematically. An excitation device 1, composed of a coil system 20 and an arrangement for applying electricity to the coil system, induces a device 2 to vibrate via a magnetic field generated by the coil system. The device 2 is placed on the object to be measured 11, the tissue, for example, by being glued on or by the use of a gel. The device 2 is composed, in this case, of a small magnet 4 and a conductive foil 3, which, according to FIG. 1, is designed to be circular in shape, with the magnet 4 being disposed in the center of the foil 3. The more or less intensive vibrations of the tissue are continued by the conductive foil 3. These vibrations are determined by means of an electrical impedance measurement device 8. The measured signals are fed into an evaluation device 10, for example, a computer system, via a lock-in amplifier 9 and are evaluated there. As the state of health of the tissue influences its elasticity, the degree of the tissue vibrations can be measured by the vibrations forced by the magnets 4 by means of the conductive foil 3. In a preferred embodiment, the mass of the actuator and the sensor are less than 0.2 g, preferably less than 0.1 g.

Figure 2:
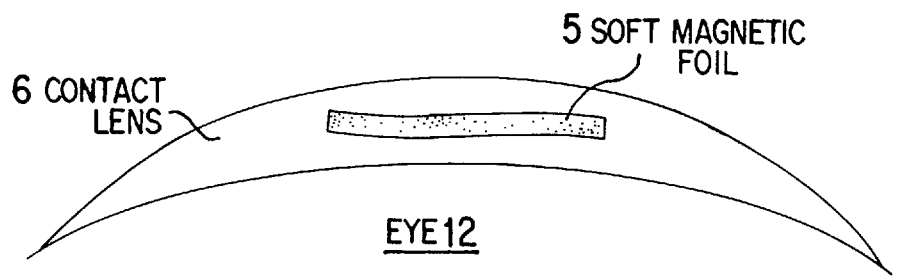
FIG. 2 shows a schematic of device 2 in FIG. 1, useful in measuring intraocular pressure.

In another embodiment, FIG. 2 shows, schematically, the measurement system for measuring intraocular pressure. For this purpose, for example, the measuring device is implanted in a contact lens 6 in such manner that it can be easily placed on the eye 12 to be examined by the physician. In this case shown in FIG. 2, permanent magnets and conductive foils are not employed, but rather a soft magnetic material, for example, a foil 5, which can be conductive or even nonconductive, is employed of course, a magnet 4 and a conductive foil 3 can, alternatively, be employed. In the event of a nonconductive foil, a conductive foil can additionally be placed on foil 5. Under some circumstances, even a soft magnetic conductive foil can be applied directly on the eye.

Figure 3:
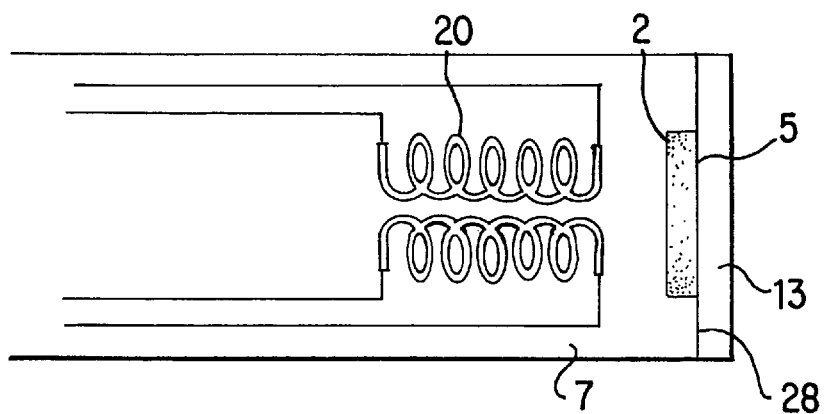
FIG. 3 shows a schematic of device 2 in FIG. 1, built into an endoscope.

In another embodiment, FIG. 3 shows the measuring system built into an endoscope 7, in which the foil 5 is disposed at the end of the endoscope or the part placed on the tissue. Part of the foil 5 is placed on the tissue. A magnet and a conductive foil can also be employed as discussed above. In order to protect the actual measuring device 2 and for one-time use of the surgical instrument, it is recommended to cover parts the measuring system parts with an elastic membrane 28. This membrane can be removed after a one-time use and replaced with a new elastic membrane. FIG. 3 shows, in addition, only the excitation coil 20 of the device, with the coil connection lines being connected to any measuring device, for example, a device for measuring impedance and exciting the coils.

In the new measuring system of the invention, the permanent magnet and/or the soft magnetic foil represents the actuator, which is induced to vibrate by means of a coil. In this manner, the object to be measured is induced to vibrate. In contrast to the device according to German patent document DE 34 33 699 A1, the sensor is a foil made of conductive material, which influences the impedance of a coil system and, therefore, permits drawing conclusions about the movement of the examined, mechanically excited tissue.

The vibrating foil modulates the impedance of the coil system on the basis of the eddy currents induced in the foil and, in the case of a soft magnetic foil, on the basis of the magnetic polarization generated in the foil. In order to induce eddy currents, the frequency with which the impedance is measured has to be correspondingly high.

In order to measure the amplitude and the phase of the vibration, the impedance of the coil system has to be measured. The impedance is measured by means of a carrier wave in a known manner. There are various alternatives. Frequency modulation occurs if the measuring coil system is the frequency determining element of an oscillator. Amplitude modulation occurs if the measuring coil is built into a measuring bridge supplied with constant voltage.

A FM demodulation is usually executed in the form of a phase lock loop (PLL) circuit. Amplitude demodulation can be executed in a simple manner by means of a rectifier and a low pass filter. However, it is better to use the supply voltage of the measuring bridge as the reference signal and then to measure the amplitude and the phase of the measuring signal by means of a two phase lock-in amplifier.

The now demodulated carrier wave of the measuring coil is fed to another lock-in amplifier, whose reference is the excitation signal. Artifacts and drift can be filtered out, because the lock-in amplifier only measures the systems response to the excitation signal.

The system is automated. A computer 10 controls the excitation frequency and reads the phase and the amplitude of the vibration of the lock-in amplifier 9. The system measures the amplitude and the phase at several excitation frequencies automatically so that a mechanical transmission function can be derived. The computer 10 can store and display the measured data. Mechanical parameters can be calculated from the function using certain algorithms.

Mechanical vibration examinations find use in the following biomedical applications, for example:

Measuring pressure

Frequently in biomedicine, pressure cannot be measured directly because the invasive nature of the measuring device forbids placing a pressure sensor in the fluid to be measured. Therefore, pressure has to be measured using less invasive alternative methods. Consequently, measuring intraocular pressure directly, continuously, and non-invasively is impossible. Invasive measurements have already been conducted (Y. Backlund, L. Rosengren, B. Hök, and B. Svedbergh, "Passive Silicon Transensor Intended for Biomedical, Remote Pressure Monitoring," Sensors and Actuators A21, pp. 5 (1990)). Various attempts have been made to measure intraocular pressure continuously by means of indirect methods U.S. Pat. No. 4,089,329; U.S. Pat. No. 4,305,399; and G. Bartsch, M. Rieder, V. Denffer, and G. Bramm, System zur kontinuierlichen Langzeittonometrie mittels Haftlinsesensor," Biomedizinische Technik Band 36 Ergänzungsband, pp. 393–394 (1991)).

In certain aspects of the invention, an apparatus and method are provided that represent a new, indirect method for continuous measurement of intraocular pressure. Intraocular pressure influences the mechanical properties of the eye exterior. Measuring these properties permits deducing information about the intraocular pressure. The advantages of the new technique become quite clear. The components of the measuring system, which are placed on the object to be measured, can be integrated in a contact lens. This is possible because wiring is obviated and the components can be miniaturized quite well.

Disease Diagnosis

Some diseases influence the mechanical properties of tissue. For example, the mechanical properties of cancerous tissue generally differs from that of healthy tissue. Skin diseases, for example, scleroderma (P. Bjerring, Skin Elasticity Measured by Dynamic Admittance a New Technique for Mechanical Measurements in Patients with Scleroderma," Acta Dermatogogica Venerologica Suppl. 120, pp. 83–87)) also change the mechanical properties of the skin. The invention can also be applied here. Due to the fact that the apparatus can be greatly miniaturized, the invention can be built into an endoscope, which was not possible with conventional mechanical measuring methods, see, for example, FIG. 3.

Although the invention has been described and illustrated in detail, it is to be clearly understood that the same is by way of illustration and example and is not to be taken as a limitation. The spirit and scope of the present invention are to be limited only by the terms of the appended claims.

What is claimed is:

1. An apparatus for measuring the mechanical properties of biological tissue comprising:
   a device for generating a magnetic field by means of a coil system;
   a device for mechanically exciting the tissue by means of a permanent magnet as the actuator and a conductive foil as a sensor; and
   a device for measuring any change in impedance, wherein said sensor is inductively coupled to said coil system.

2. An apparatus according to claim 1, wherein the mass of said actuator and said sensor is less than approximately 0.2 g.

3. An apparatus according to claim 1, wherein the apparatus is operably connected to an endoscope and said conductive foil being designed as the distal end of the endoscope.

4. An apparatus according to claim 3, further comprising an elastic foil disposed between the tissue to be examined and said conductive foil.

5. An apparatus according to claim 1, the foil, the magnet, or both being operably embedded in a contact lens.

6. A method for measuring the mechanical properties of biological tissue comprising operably contacting the apparatus of claim 1 to said tissue and measuring the responses.

7. A method as claimed in claim 6, wherein the mechanical property to be measured is intraocular pressure.

8. A method as claimed in claim 6, wherein the biological tissue is skin.

9. A method as claimed in claim 6, wherein the apparatus of claim 1 is operably connected to an endoscope.

10. A method as claimed in claim 6, wherein the apparatus of claim 1 is operably connected to an endoscope.

11. An apparatus for measuring the mechanical properties of biological tissue comprising:
    a device for generating a magnetic field by means of a coil system;
    a device for mechanically exciting the tissue by means of a foil comprising a soft magnetic material; and
    a device for measuring any change in impedance,
    wherein said foil comprising a soft magnetic material is capable of acting as an actuator and is simultaneously designed as a sensor for measuring the mechanical vibrations of the tissue, and wherein said sensor is inductively coupled to said coil system.

12. An apparatus according to claim 2, further comprising a conductive foil placed on said soft magnetic foil.

13. An apparatus according to claim 11, wherein the mass of said actuator and said sensor is less than approximately 0.2 g.

14. An apparatus according to claim 11, wherein the apparatus is operably connected to an endoscope and said soft magnetic material foil being designed as the distal end of the endoscope.

15. An apparatus according to claim 14, further comprising an elastic foil disposed between the tissue to be examined and said soft magnetic material foil.

16. An apparatus according to claim 11, the foil comprising the soft magnetic material being operably embedded in a contact lens.

17. A method for measuring the mechanical properties of biological tissue comprising operably contacting the apparatus of claim 2 to said tissue and measuring the responses.

18. A method as claimed in claim 17, wherein the mechanical property to be measured is intraocular pressure.

19. A method as claimed in claim 17, wherein the biological tissue is skin.

20. An apparatus for measuring the mechanical properties of biological tissue, comprising:
    a soft magnetic material capable of simultaneously acting as an actuator to mechanically excite the tissue and as a sensor of the vibrations in the tissue;
    a magnetic field generator; and
    an impedance recorder;
    wherein the apparatus may be placed on a biological tissue.

21. An apparatus for measuring mechanical properties of biological tissue, comprising:
    an excitation system;
    a mechanical actuator and sensor adaptable to contact the biological tissue, said mechanical actuator and sensor wirelessly coupling with said excitation system; and
    an impedance measuring system which measures any change in impedance of said sensor.

* * * * *